(12) United States Patent
Venturini et al.

(10) Patent No.: US 11,229,463 B2
(45) Date of Patent: Jan. 25, 2022

(54) BONE PLATE FOR EPIPHYSIODESIS

(71) Applicant: ORTHOFIX S.R.L., Bussolengo (IT)

(72) Inventors: Daniele Venturini, Povegliano Veronese (IT); Marco Magni, Ferrara (IT); Andrea Zaccaria, Tregnago (IT)

(73) Assignee: ORTHOFIX S.R.L., Bussolengo (IT)

( * ) Notice: Subject to any disclaimer, the term of this patent is extended or adjusted under 35 U.S.C. 154(b) by 255 days.

(21) Appl. No.: 16/303,883

(22) PCT Filed: Jun. 1, 2017

(86) PCT No.: PCT/EP2017/063332
§ 371 (c)(1),
(2) Date: Nov. 21, 2018

(87) PCT Pub. No.: WO2017/215938
PCT Pub. Date: Dec. 21, 2017

(65) Prior Publication Data
US 2020/0323572 A1 Oct. 15, 2020

(30) Foreign Application Priority Data
Jun. 17, 2016 (EP) ..................................... 16425060

(51) Int. Cl.
*A61B 17/80* (2006.01)
(52) U.S. Cl.
CPC ...... *A61B 17/8061* (2013.01); *A61B 17/8014* (2013.01)
(58) Field of Classification Search
CPC .................................................... A61B 17/80
(Continued)

(56) References Cited

U.S. PATENT DOCUMENTS 7,695,472 B2 * 4/2010 Young ................ A61B 17/8052
606/70
8,029,507 B2 10/2011 Green et al.
(Continued)

FOREIGN PATENT DOCUMENTS

CA 2723643 A1 * 5/2012 ............. A61B 17/80
FR 2 922 094 A1 4/2009

OTHER PUBLICATIONS

European Patent Office, "Search Report" in application No. PCT/EP2017/063332, dated Sep. 18, 2018, 8 pages.
(Continued)

*Primary Examiner* — Matthew J Lawson
*Assistant Examiner* — Lisa Nguyen
(74) *Attorney, Agent, or Firm* — Hickman Becker Bingham Ledesma LLP; Malgorzata A. Kulczycka

(57) ABSTRACT

The present invention relates to a bone plate (1, 21) for epiphysiodesis, which has been advantageously improved to allow better articulation of the fixing screws engaged with the bone plate (1, 21), comprising: a first portion (4) and a second portion (6) joined by a connecting portion (5), intersected by a first (9) and a second opening (10), respectively, structured to receive the same number of fixing screws; the bone plate having a bilobal figure, such as an eight shape; at least one of said first (9) and second (10) openings comprising: a cup-shaped seat (12) for housing a fixing screw head in a tillable manner, and at least one recess (14") which merges into the cup-shaped seat (12) expanding an exit section (12*b*) away from the connecting portion (5).

7 Claims, 14 Drawing Sheets

(58) Field of Classification Search
USPC .................................................. 606/280–299
See application file for complete search history.

(56) References Cited

U.S. PATENT DOCUMENTS

| | | | |
|---|---|---|---|
| 2002/0183752 A1* | 12/2002 | Steiner ............... | A61B 17/8014 606/282 |
| 2004/0111089 A1 | 6/2004 | Stevens et al. | |
| 2008/0015593 A1 | 1/2008 | Pfefferle et al. | |
| 2008/0161816 A1* | 7/2008 | Stevens .............. | A61B 17/1728 606/87 |
| 2008/0200955 A1 | 8/2008 | Tepic | |
| 2010/0004691 A1 | 1/2010 | Amato et al. | |

OTHER PUBLICATIONS

European Patent Office, "Search Report" in application No. PCT/EP2017/063332, dated Sep. 15, 2017, 4 pages.

\* cited by examiner

BONE PLATE FOR EPIPHYSIODESIS

FIELD OF APPLICATION

The present invention relates to an implantable device for correcting angular deformities of long bones, such as genu varum and genu valgum, and in particular a bone plate for epiphysiodesis operations applied at the ends of deformed bones in paediatric patients.

The invention can therefore be applied mainly in the paediatric orthopaedics field, and the following description is made with reference to, but not limited to, use within this field.

PRIOR ART

In the technical sector relating to this invention, the use of staples or plates is recognised for limiting or impeding growth at a particular point of the growth plate at the end of a long bone with an angular deformity in paediatric patients. The physiological process of physeal tissue growth, which remains unhindered on the opposite, non-instrumented side, promotes gradual axial realignment of the bone.

In the specific case of using a bone plate, the plate is positioned using fixing screws which fasten it to the epiphysis and the metaphysis on the convex surface of the deformed bone.

The bone plate is therefore composed of a metaphyseal portion and an epiphyseal portion, which are fastened to the metaphysis and epiphysis respectively, joined by a connecting portion positioned at the growth plate. The metaphyseal and epiphyseal portions both have at least one through hole to accommodate said fixing screw.

In a generally used embodiment, the fixing screws are loosely fastened in said holes so that their angle can gradually alter to adapt to the bone growth process.

In particular, the fixing screw preferably has a spherical head structured to be positioned, in a tiltable manner, within a spherical housing which opens at the outer end (i.e. opposite the bone site) of the through hole.

As mentioned above, as the physeal tissue grows the fixing screws are subject to a dragging action which causes a gradual angular divarication, i.e. the two screws tilt away from the median plane passing through the growth plate.

Although this is advantageous in several respects, and essentially meets the current needs of the industry, the bone plates for epiphysiodesis in the prior art nevertheless have certain drawbacks which are unresolved to date and which are identified below.

A significant drawback relates in particular to the risk of the fixing screws breaking during the bone realignment process.

In fact, once the maximum permissible angular divarication has been reached, the shank reaches an abutment position against the lower edge of the hole. This causes a bending stress that can lead to breakage of the screw.

In fact, in some cases, the angle permitted by the screws is not sufficient to ensure full correction of the bone deformity with a single surgery, and the screws must be repositioned once they have reached the abutment position previously identified.

Currently, the technical solutions taken to counter the above drawbacks enable the bone plate to distort in order to follow the divarication movement of the screws.

One such solution, presented in U.S. Pat. No. 8,029,507, involves the use of a mechanical hinge at the connecting portion of an otherwise rigid bone plate. Moreover, as well as a remarkable increase in manufacturing costs, this solution presents further disadvantages related to the lateral projection of the hinge element, which defines an additional encumbrance of the device as this can trigger an inflammatory process in the surrounding soft tissue.

Another solution, presented in US2004/111089A1, relates to a bone alignment implant having a bilobal figure of eight shape. The implant includes a first bone fastener with a first bone engager that is adapted for fixation into the metaphyseal bone and a second bone fastener with a second bone engager that is adapted for fixation into the diaphyseal bone. A link connecting the two fasteners spans across the physis. These implant acts as flexible tethers between the metaphyseal and the diaphyseal sections of bone during bone growth.

Another solution, presented in FR2922094B1, relates to an osteosynthesis plate, comprising a central hole for receiving a screw (6). A recess communicates with the central hole and has certain depth to receive a conical portion of the screw. The conical portion is the head of the screw, which is in contact with a machine portion of the bone when the plate is applied.

Another solution, presented in US2008/015593A1, relates to a bone plate having plate holes whose hole axis runs obliquely in relation to the underside of the plate, according to a predetermined direction. A bone screw, which is screwed into the plate hole, can be blocked in the plate hole at an angle selected from a predefined angle range.

Another solution, presented in US2008/200955A1, relates to a plate for treatment of bone fractures, with annular recesses surrounding the screw holes at the lower, bone facing surface of the plate and transverse grooves between the holes. These annular recesses require complex machining and may hinder plate resistance and compactness.

A technical problem underlying the present invention is, therefore, that of devising a bone plate for epiphysiodesis which solves at least some of the disadvantages described above with reference to the prior art, and which, in particular, avoids or limits the need for repositioning operations whilst preventing any failure of the implant.

SUMMARY OF THE INVENTION

The solution idea underlying the present invention is to locally expand the screws housing openings by means of specific recesses.

The previously defined technical problem is therefore solved by a bone plate for epiphysiodesis comprising: a first portion and a second portion structured to be fastened to the epiphysis and metaphysis, respectively, of a long bone in a paediatric patient; said first and second portions being joined by a connecting portion structured to straddle the growth plate of said long bone; said first and said second portions being intersected by at least a first and at least a second opening, respectively, structured to receive the same number of fixing screws for fastening to said long bone; said bone plate having a bilobal figure, such as an eight shape; at least one of said first and second openings comprising: a cup-shaped seat for housing the head of said fixing screw in a tiltable manner, said cup-shaped seat having an entry section structured to allow the insertion of said fixing screw head and an exit section of an at least locally smaller size compared to a respective size of said entry section so as to retain said fixing screw head; and at least one recess which merges into the cup-shaped seat expanding the exit section away from the connecting portion.

As a person skilled in the art will easily understand, the presence of the recess allows the side abutment point to move away from the orthogonal axis of the first position of the screw, enabling the permissible divarication range to be significantly increased while maintaining a simple and relatively cheap manufacturing process.

Preferably, both the first and the second openings have the advantageous characteristic of the recess which merges with the cup-shaped seat, thus improving the divarication range of both screws. In particular, said bone plate is preferably symmetrical, so that said first and second openings are identical and opposite each other.

At least one of said first and second openings further comprises a cylindrical through hole which extends said cup-shaped seat beyond said exit section opening on a first surface of the bone plate on the opposite side to a second surface on which said cup-shaped seat opens.

Alternatively, the exit section of the cup-shaped seat can open directly onto said first surface.

Preferably, said cup-shaped seat has a spherical inner shape, shaped to slidably house a fixing screw head, which is also spherical.

Other shapes which allow the relevant motion of the screw head can be used in the context of the present invention.

In certain embodiments, said recess can take the form of a hole, for example a cylindrical or conical hole, which locally widens an outer periphery, opposite the connecting portion, of the exit section of said cup-shaped seat.

In particular, said recess can take the form of an eccentric hole parallel to a central axis of symmetry of said cup-shaped seat. Said hole is preferably tangent to the entry section of the cup-shaped seat. Said hole is preferably cylindrical in shape, with a smaller diameter than the entry section of the cup-shaped seat.

In an alternative embodiment, said recess can take the form of a tilted hole with respect to a central axis of symmetry of said cup-shaped seat, which extends from a merging point on said cup-shaped seat away from both the connecting portion and the entry section.

In another alternative embodiment, said recess can take the form of a hollow, opens on a first surface of the bone plate opposite a second surface on which said cup-shaped seat opens, with a depth less than the thickness of said bone plate, said hollow extending away from said connecting portion from a merging point in said cup-shaped seat. Said hollow has preferably the same width as the diameter of the exit section of the cup-shaped seat in which it merges.

The cup-shaped seat for housing the head of the fixing screw, according to the present invention, allows a larger clearance between the bone plate and the boring tool, in particular during preparation of the hole. Advantageously, the bone plate according to the present invention allows for larger freedom to the surgeon, who gains better access to the surgery area without risk of damaging the plate with the surgical tools. The plate according to the present invention is preferably made from a single piece of rigid, non-pliable material, for example a biocompatible material such as titanium.

The aforementioned technical problem is also solved by an epiphysiodesis kit comprising a bone plate as described above and two fixing screws with a head which can be inserted into said cup-shaped seat in a tiltable manner and a shank which is at least partially threaded and structured to pass through said first or said second opening, respectively, to engage with the epiphysis or metaphysis respectively of the patient. In particular, the head of said screw can be spherical and able to enter a respective spherical seat.

The previously defined technical problem is also solved by a method for manufacturing a bone plate of the type described above, comprising at least the following stages:

preparing a flat element with a first portion and a second portion joined by a connecting portion;

making said first opening on said first portion and said second opening on said second portion;

wherein at least one of said first and said second openings (preferably both) is made by:

forming said cup-shaped seat;

subsequently expanding, by means of machining, said cup-shaped seat to form said recess.

The characteristics and advantages of the device and the method according to the invention will be apparent from the following descriptions of some examples of embodiments, provided in non-limiting manner with reference to the attached drawings.

DETAILED DESCRIPTION

Figure 1A:
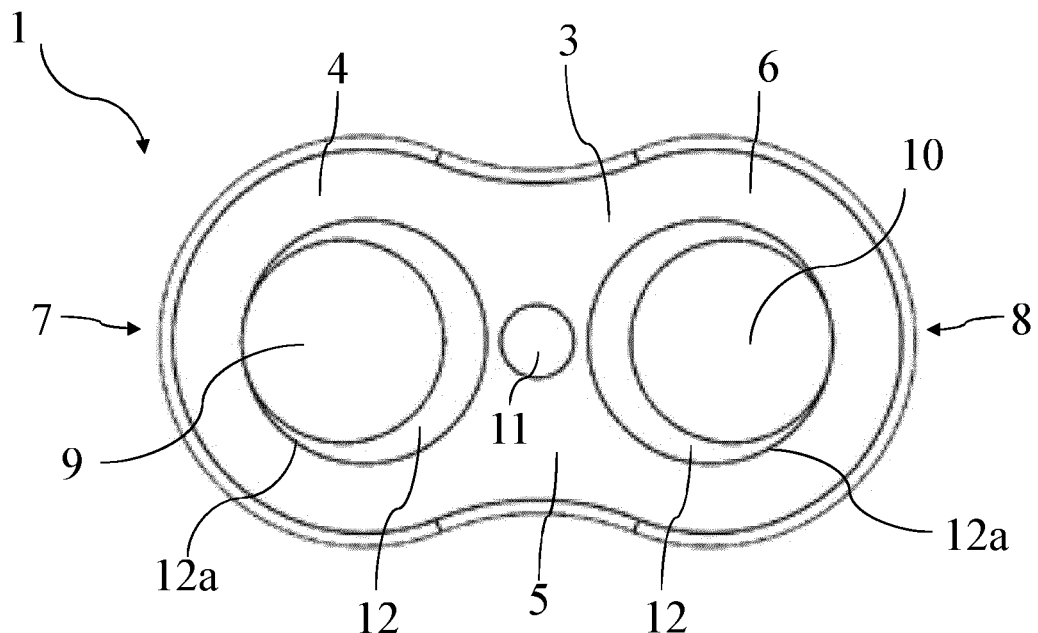
FIG. 1A is a top view of a bone plate according to a first embodiment.
Figure 1B:
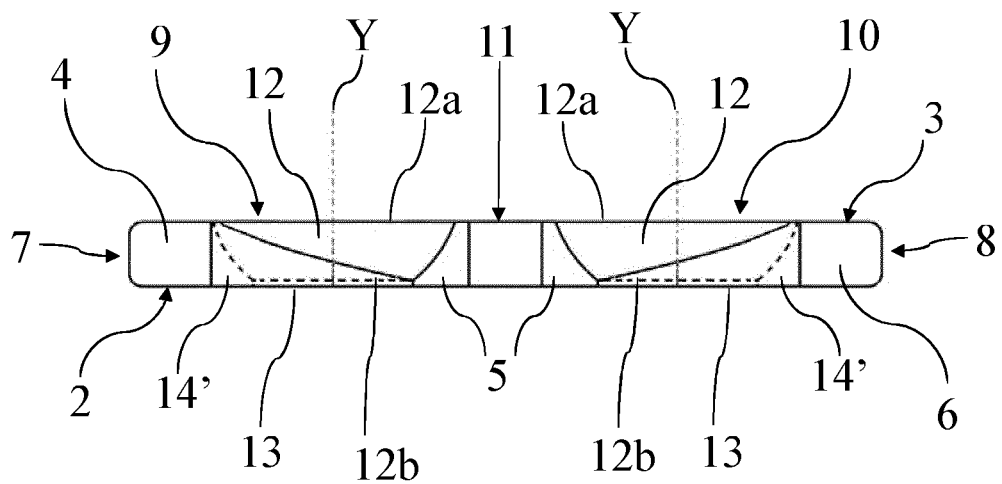
FIG. 1B is a sectional side view of the bone plate in FIG. 1A.

With reference to these figures, a bone plate 1 for epiphysiodesis is globally and schematically indicated.

This bone plate 1, preferably made from a rigid, biocompatible material (such as titanium), is a bilobal, figure of eight shape, with an even thickness, developing along a longitudinal direction which is greater than a transversal direction. The bone plate 1 has two opposing surfaces, the first of which is suitable for being placed in contact with the bone surface; for the sake of simplicity, for the remainder of this description said first surface will be referred to as the bottom surface 2 and the second surface opposite it will be referred to as the top surface 3 of the bone plate 1.

Any references made to position in the description, including indications such as upper or lower, above or below, or similar wordings, will always refer to the orientation of the surfaces as stated above, corresponding to what is described in FIGS. 1B, 2B, 3B and 4B.

The bilobal bone plate 1 comprises a first portion 4 and a second portion 6 structured to be fastened to the epiphysis and metaphysis, respectively, of a long bone in a paediatric patient presenting an angular deformity which may be corrected by means of a bone plate 1.

The first 4 and second 6 portions are connected by a connecting portion 5, at which point there is a localised narrowing of the bone plate 1. Said connecting portion 5 has a guide through hole 11 which facilitates positioning the bone plate 1 in such a way that the connecting portion 5 straddles the growth plate between the epiphysis and the metaphysis.

The bone plate 1 is symmetrical in relation to a transverse plane passing through the centre of the connecting portion 5.

The areas of the first 4 and second 6 sections positioned at the greatest distance from the transverse plane passing through the centre of the connecting portion 5, respectively determine a first end 7 and a second end 8 of the bone plate 1.

The first portion 4 is intersected by a first hole 9 structured to receive a fixing screw 15.

The second portion 6 is intersected by a second hole 10 structured to receive a fixing screw 15. The symmetry of the bone plate 1 means that portions 4 and 6 can be fastened equally to the epiphysis and metaphysis.

As disclosed above, the bone plate has a bilobal figure, in particular an eight shape.

Figure 6:
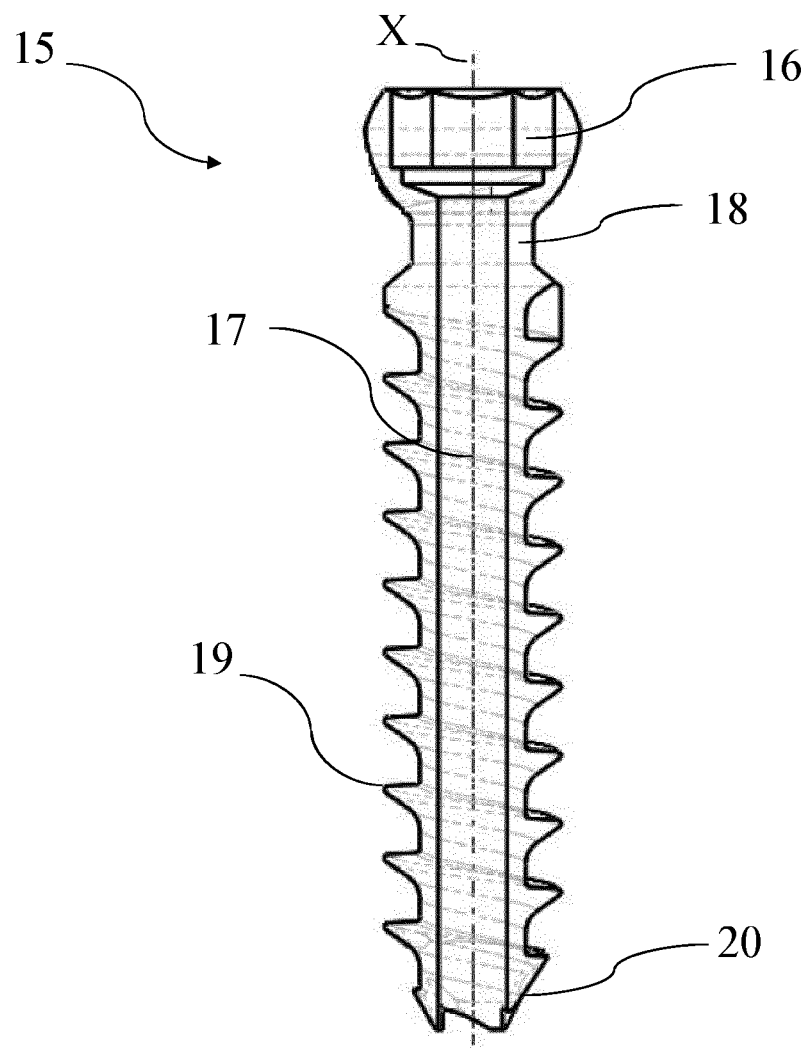
FIG. 6 is a sectional side view of the fixing screw.

In one of its preferred embodiments, the fixing screw 15, detailed in FIG. 6, comprises a head 16, which is preferably spherical, positioned at the end of a straight shank on a longitudinal axis X. The shank has a non-threaded portion 18 just before the head, then a threaded portion 19, preferably a v-thread, and a self-tapping tip 20 at the opposite end to the head 16. The shank is passed through by an inner guide cannula 17 which opens on a hexagonal recess inside the head 16.

By virtue of the above symmetry of the bone plate 1, the first opening 9 and the second opening 10 are identical and opposite each other; for the sake of simplicity the following describes the internal shape of a generic opening 9 or 10, and this description applies to both of said openings.

The opening 9, 10 comprises: a cup-shaped seat 12, preferably hemispherical, for housing the head 16 of the fixing screw 15 in a tiltable manner; a cylindrical hole 13, which opens in the bottom of said cup-shaped seat 12, structured to house the shank of the fixing screw 15; and at least one recess 14', 14", 14'", 14"" which merges into the cup-shaped seat 12 and the cylindrical hole 13.

The cup-shaped seat 12 defines a spherical coupling with the head 16 housed in it, enabling the shank of the screw 15 to move freely. In particular, the fixing screw 15 can tilt on a longitudinal plane to the bone plate 1, away from the median plane passing through the growth plate, until it reaches an abutment or stop point.

The cup-shaped seat 12 comprises in particular: an entry section 12a, preferably circular, structured to allow the insertion of the head 16 of a fixing screw 15 into the opening 9, 10, and an exit section 12b of an at least locally smaller size compared to a respective size of the entry section 12a so that it can retain the head 16 of the fixing screw 15 within the cup-shaped seat 12.

The cup-shaped seat 12 is preferably hemispherical in shape, with axis Y orthogonal to the bone plate 1 and passing though the centre of the entry section 12a.

The cylindrical hole 13 extends coaxially to the cup-shaped seat 12, and has a diameter equal to that of the exit section 12b.

The recess 14', 14", 14'", 14"" merges into the cup-shaped seat 12 causing a widening of the exit section 12b away from the connecting portion 5.

The opening 9, 10 in the bone plate 1, whose internal geometry has been described above, is manufactured according to the following stages:

preparing a flat element with a first portion 4 and a second portion 6 joined by a connecting portion 5;

making the first opening 9 on said first portion 4, and the second opening 10 on said second portion 6;

wherein at least one of said first and said second openings is made by:

forming the cup-shaped seat 12, preferably spherical, by means of machining (for example, boring with subsequent slotting);

making a cylindrical, straight through hole 13 below the cup-shaped seat 12 whose diameter matches the exit section 12b of the cup-shaped seat 12 which it is positioned in line with (obtained by means of the boring operation previously described);

subsequent machining in order to expand the exit section 12b of the cup-shaped seat 12 and the cylindrical hole 13 away from the connecting portion 5 by means of a recess 14', 14", 14'", 14"".

In FIGS. 1B, 2B, 3B and 4B, dotted lines indicate the profile of the cup-shaped seat 12 before the recess 14', 14", 14'", 14"" is formed.

Below, four alternative embodiments of the bone plate 1 according to the present invention are described, each of which has a differently shaped recess 14', 14", 14'", 14"" and a respective and specific manufacturing stage.

In the descriptions of these variations, identical or functionally similar elements and characteristics are identified by the same numerical references used previously, and reference is made to the preceding text for their descriptions.

By virtue of the above symmetry of the bone plate 1, for the sake of simplicity, the various embodiments are described with reference to a generic opening 9 or 10.

A first embodiment described in FIGS. 1A-1E shows a recess hereafter referred to as an eccentric recess 14'.

The eccentric recess 14' is defined by a hole, with a parallel axis and a diameter which is smaller than that of the entry section 12a of the cup-shaped seat 12. The hole is tangent to the outermost edge (i.e. closer to the respective end 7, 8 of the first 9 and second opening 10) of said entry section 12a.

The hole of the eccentric recess 14' therefore defines a cylindrical widening, orthogonal to the bone plate 1, of the external periphery of the cup-shaped seat 12a, also defining an eccentric widening of the cylindrical hole 13 which in this embodiment is completely contained in the geometry of recess 14'.

Said eccentric recess 14' is created by means of boring and slotting, creating a cylindrical through hole with a diameter which is smaller than that of the entry section 12a, with an axis parallel to axis Y of the cup-shaped seat 12, and being tangent, in the area of the connecting portion 5, to the cylindrical hole 13 of opening 9, 10 and, in the area of the respective end 7, 8, to the entry section 12a of the cup-shaped seat 12.

A second embodiment described in FIGS. 2A-2E shows a recess hereafter referred to as a slot-shaped recess 14".

The slot-shaped recess 14" is defined by a hollow which has a depth lower than the bone plate 1 thickness, and which extends lengthways from one point on the plate at one end 7, 8 to merge with the channel defined by the cup-shaped seat 12 and the cylindrical hole 13. The width of said hollow is preferably the same as the diameter of the cylindrical hole 13 that it connects with.

The slot-shaped recess 14" is formed by removing material from the area surrounding the cup-shaped seat 12 at the end 7, 8. Such removal of material is achieved by means of face milling the bone plate 1 so as to create a lengthways hollow with semi-circular end which extends from the area close to the end 7, 8 and merges in the cup-shaped seat 12 and the cylindrical hole 13 below.

Figure 3A:
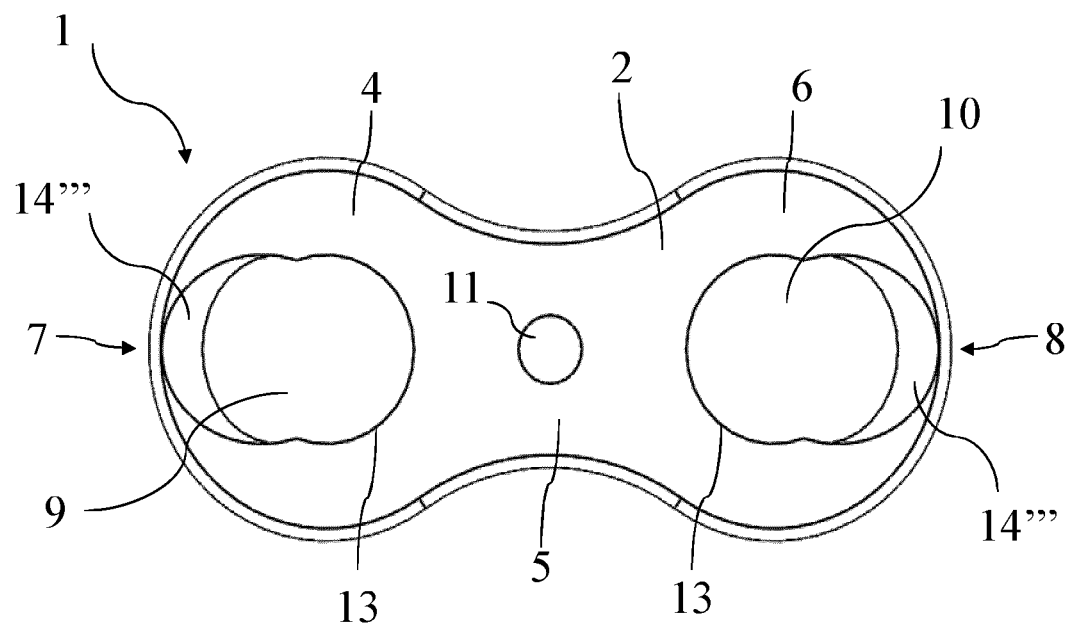
FIG. 3A is a bottom view of a bone plate according to a third embodiment.
Figure 3B:
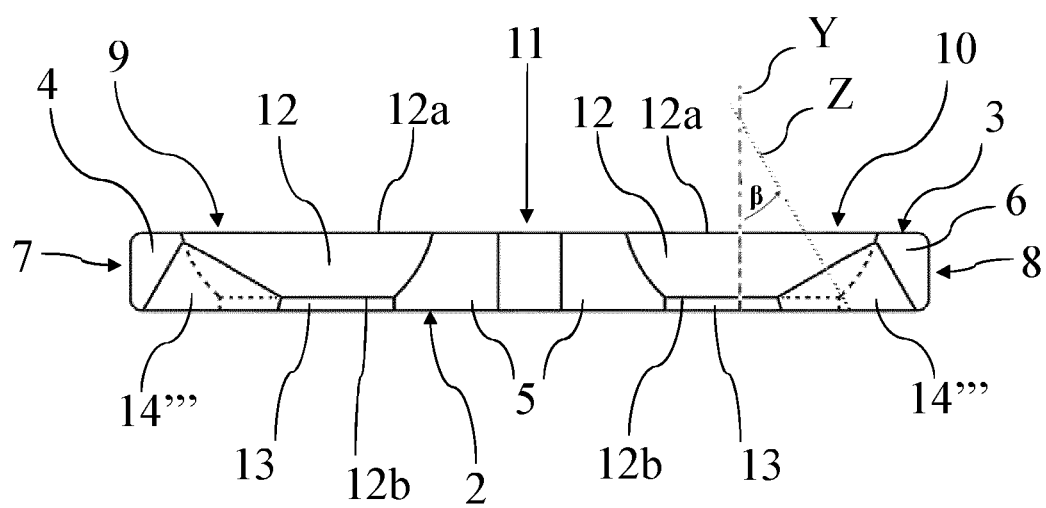
FIG. 3B is a sectional side view of the bone plate in FIG. 3A.
Figure 3C:
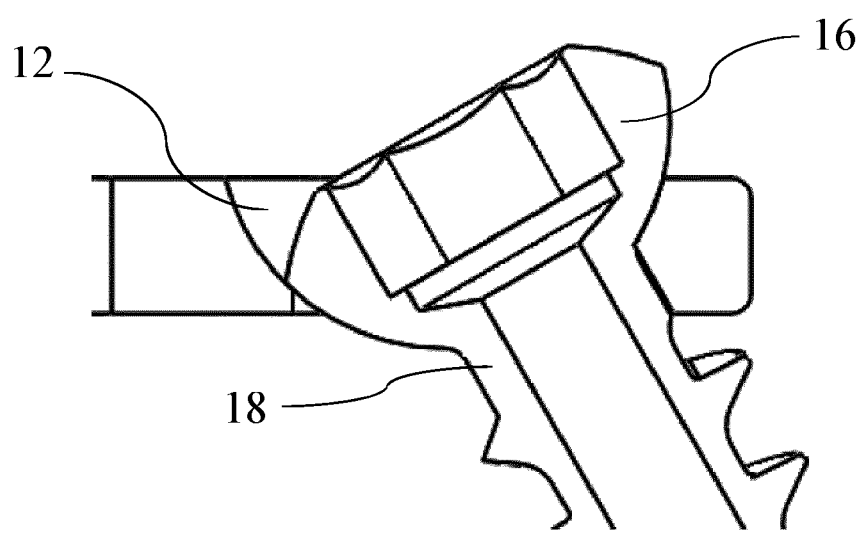
FIG. 3C is a part of FIG. 3B detailing the screw head housed within the plate.
Figure 4A:
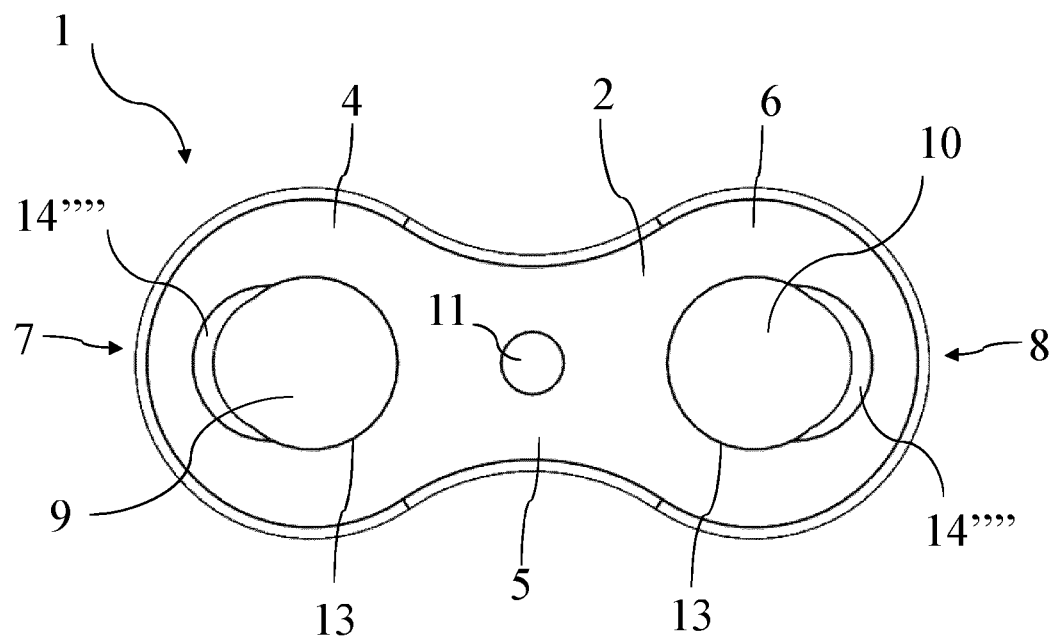
FIG. 4A is a bottom view of a bone plate according to a fourth embodiment.
Figure 4B:
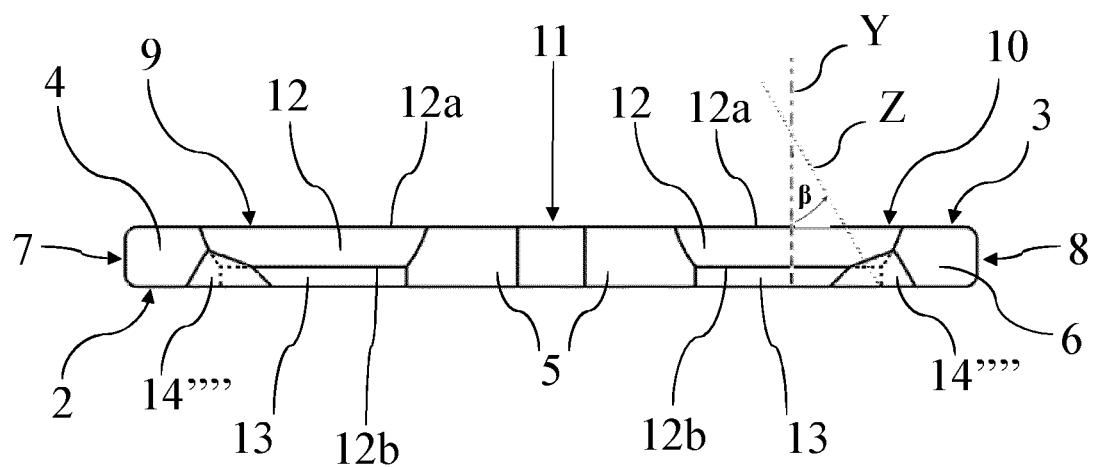
FIG. 4B is a sectional side view of the bone plate in FIG. 4A.
Figure 4C:
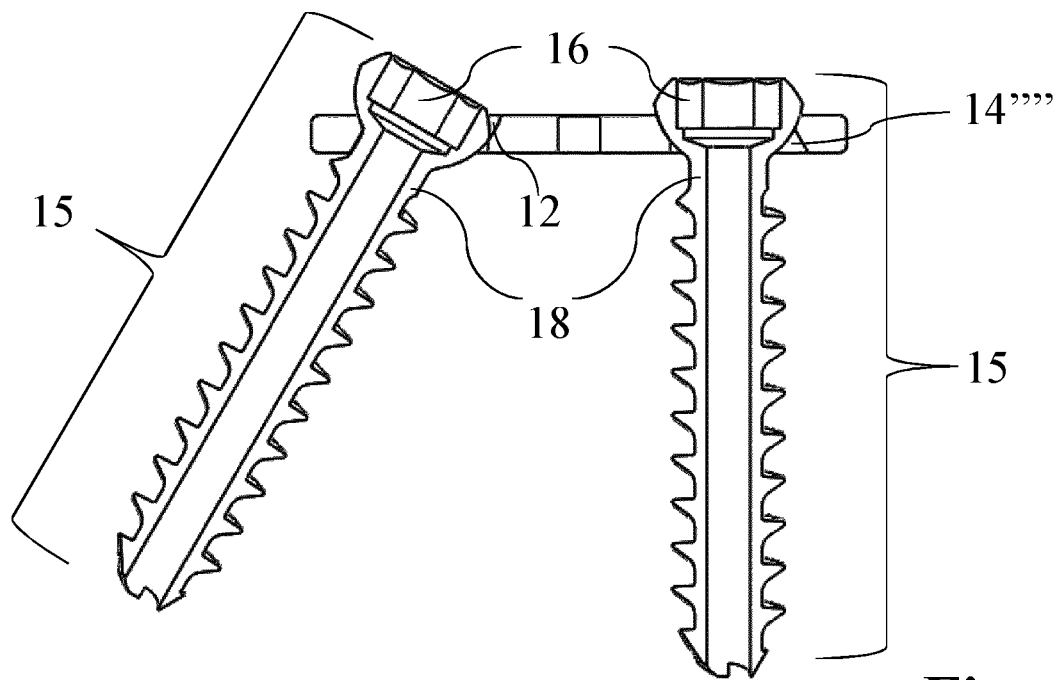
FIG. 4C is a sectional side view of the bone plate in FIG. 4A with both fixing screws inserted in a first configuration.
Figure 4D:
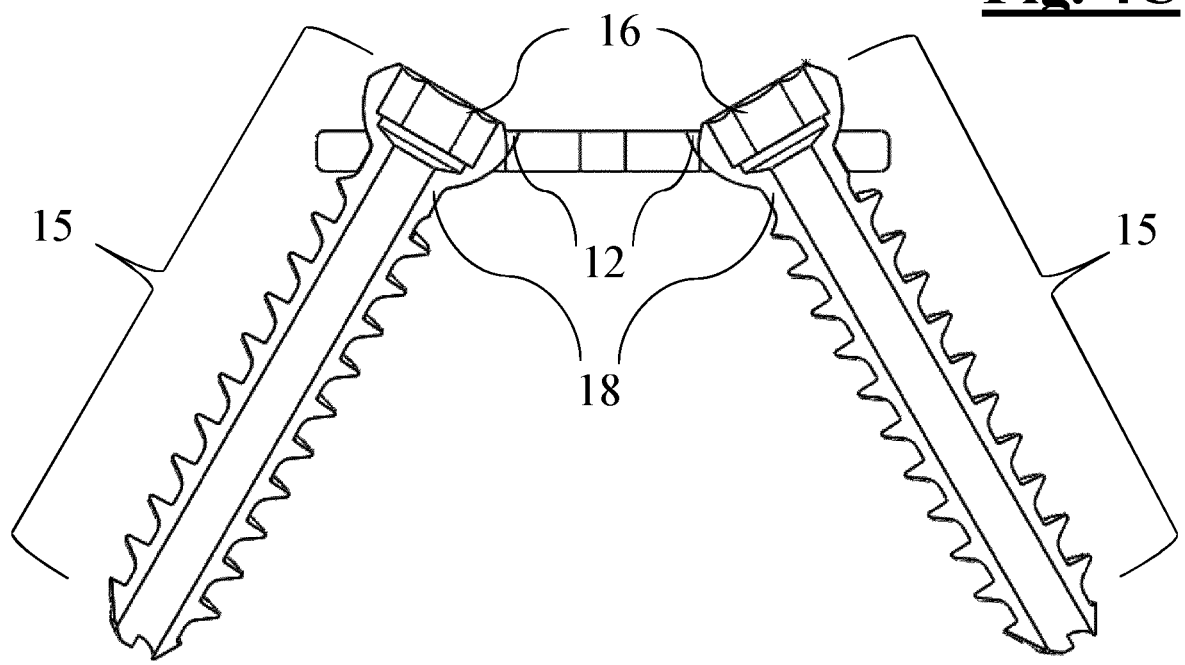
FIG. 4D is a sectional side view of the bone plate in FIG. 4A with both fixing screws inserted in a second configuration.
Figure 4E:
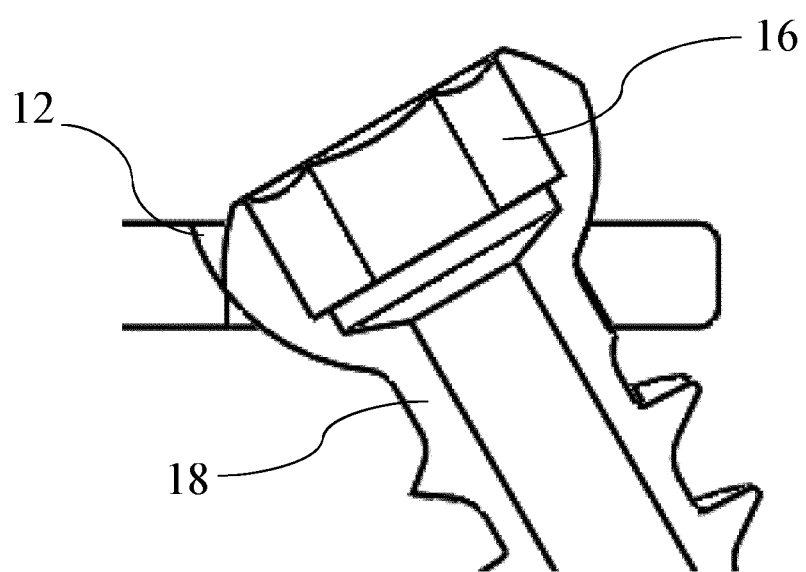
FIG. 4E is a part of FIG. 4D detailing the screw head housed within the plate.

A third embodiment described in FIGS. 3A-3C shows a recess hereafter referred to as a tilted cylindrical hole recess 14'''.

The tilted cylindrical hole recess 14''' is defined by a hole which merges within the cup-shaped seat, whose diameter is greater or at least the same as the diameter of the top non-threaded section 18 of the shank of the fixing screw 15 and which has an axis Z tilted by angle β with respect to axis Y of the opening 9, 10. The hole opens on the outer side periphery of the cup-shaped seat 12 and extends downwards and outwards, i.e. towards the respective end 7, 8, and emerges on the bottom surface 2 of the plate. The hole is merged with the cylindrical hole 13 for its entire length.

The tilted cylindrical hole recess 14''' is formed by removing material from the area surrounding the cup-shaped seat 12 at the end 7, 8 by means of a boring operation.

A fourth embodiment described in FIGS. 4A-4E shows a recess hereafter referred to as a tilted conical hole recess 14''''.

The tilted conical hole recess 14'''' is quite similar to the tilted cylindrical hole recess 14''' described above; however, the hole which defines the recess has a conical profile, and is preferably tapered towards the bottom rather than being cylindrical.

This recess 14'''' is also formed by removing material from the area surrounding the cup-shaped seat 12 at the end 7, 8 by means of a boring operation.

Figure 5A:
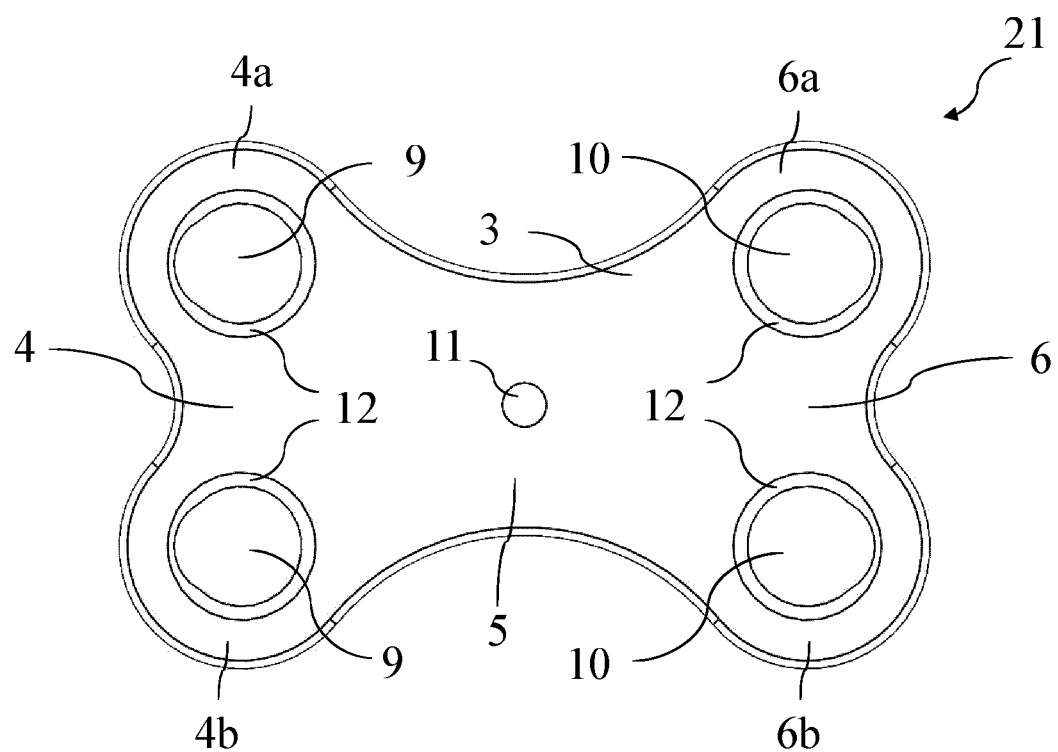
FIG. 5A is a top view of a quatrefoil version of the bone plate in FIG. 4A.
Figure 5B:
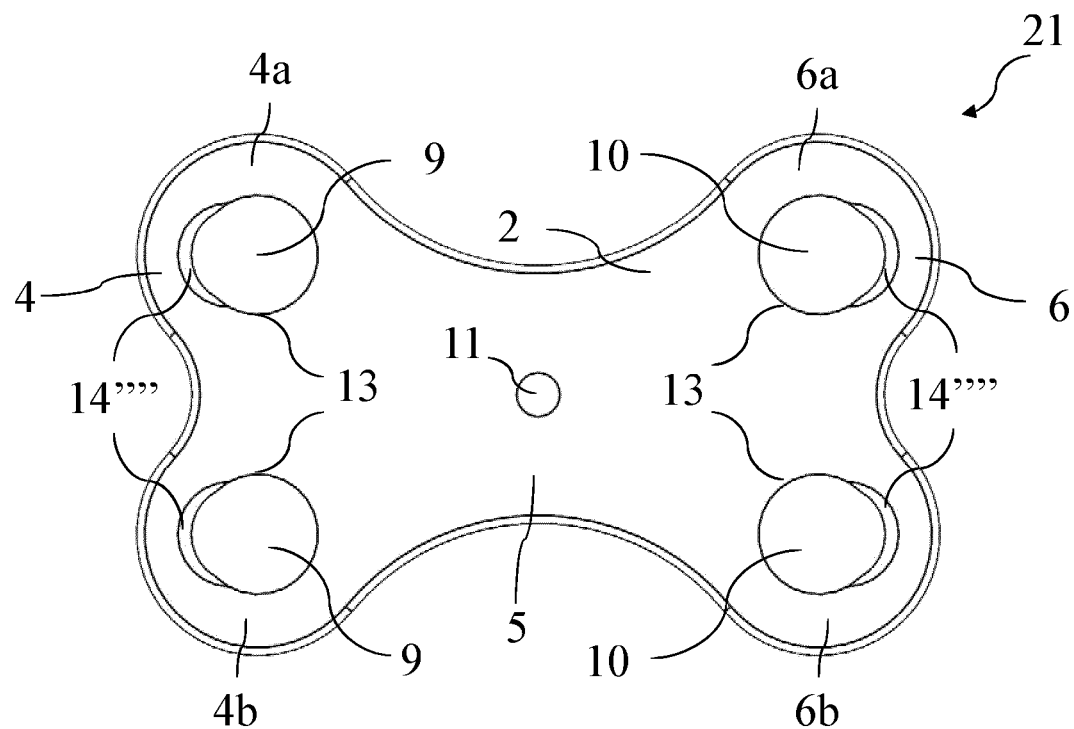
FIG. 5B is a bottom view of a quatrefoil version of the bone plate in FIG. 4A.
Figure 5C:
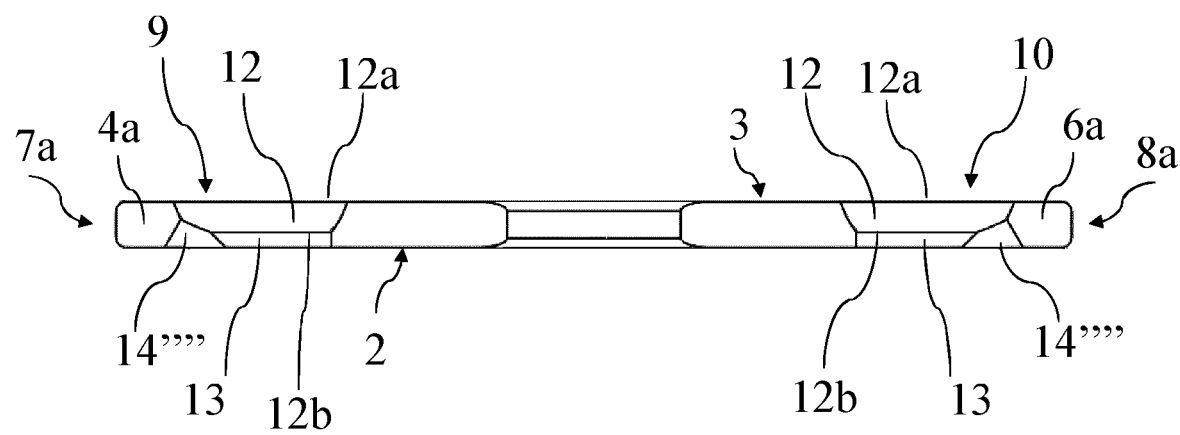
FIG. 5C is a sectional side view of the bone plate in FIG. 5A, 5B.

With particular reference to FIGS. 5A-5C, the following describes an alternative embodiment of the bone plate, which still falls within the scope of the present invention, identified by numerical reference 21.

The bone plate 21 differs from the previously described embodiment in that it is a quatrefoil where each of the sections 4, 6 has two openings 9, 10.

The quatrefoil shape, as the skilled in the art realizes, corresponds to a bilobal figure, wherein each equivalent lobe 4, 6 comprises two lobes, 4a, 4b and 6a, 6b respectively, each comprising a respective opening 9 or 10.

In particular, the first portion 4 and the second portion 6 both have two lobes, 4a, 4b and 6a, 6b respectively, adjacent to each other and symmetrical along a line of symmetry which runs the length of the bone plate 21.

Each of the two lobes 4a, 4b is intersected by a first hole 9 structured to receive a fixing screw 15.

Each of the two lobes 6a, 6b is intersected by a second hole 10 structured to receive a fixing screw 15.

By virtue of the symmetry of the bone plate 21, the first opening 9 and the second opening 10 are identical and opposite each other, i.e. the first opening 9 on lobe 4a is identical to and opposite the second opening on lobe 6a; likewise, the first opening 9 on lobe 4b is identical to and opposite the second opening on lobe 6b.

By way of example, FIGS. 5A-5C show the bone plate 21 in which said first and second openings 9, 10 are made according to the embodiment which uses a tilted conical hole recess 14''''.

Any form of the recess 14', 14", 14''', 14'''', or other similar variation, may be created at the opening 9, 10 of the bone plate 21.

The use of a quatrefoil-shaped bone plate 21 enables the bone plate to be fixed to the bone more securely using two fixing screws inserted at both the metaphysis and the epiphysis.

Alternative embodiments with a greater number of openings than the four described above, wherein one or more of the openings has a recess, are included in the present invention despite not being explicitly described in the present application.

Implanting the bone plate 1 requires the use of a guide wire which is inserted through the guide hole 11 to locate the growth plate and guide the alignment of the bone plate 1 at the implantation site.

Preferably, another two guides are inserted through the openings 9 and 10, at the epiphysis and metaphysis respectively of the end of the bone being treated.

The fixing screws 15 are inserted into the openings 9, 10 to secure the bone plate 1 to the bone by moving the fixing screws 15 along said guides, using the inner guide cannula 17.

Figure 1C:
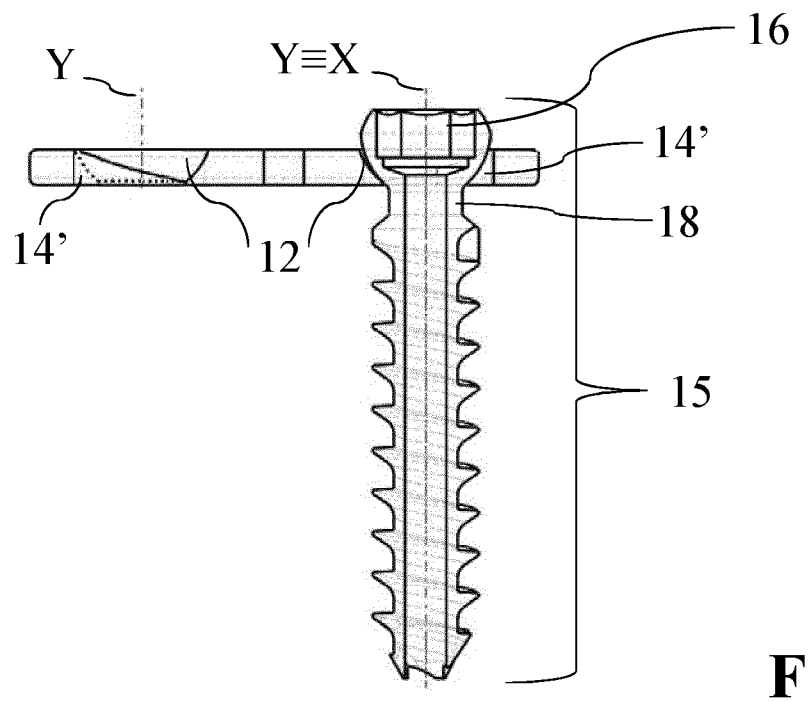
FIG. 1C is a sectional side view of the bone plate in FIG. 1A with a fixing screw inserted in a first configuration.
Figure 1D:
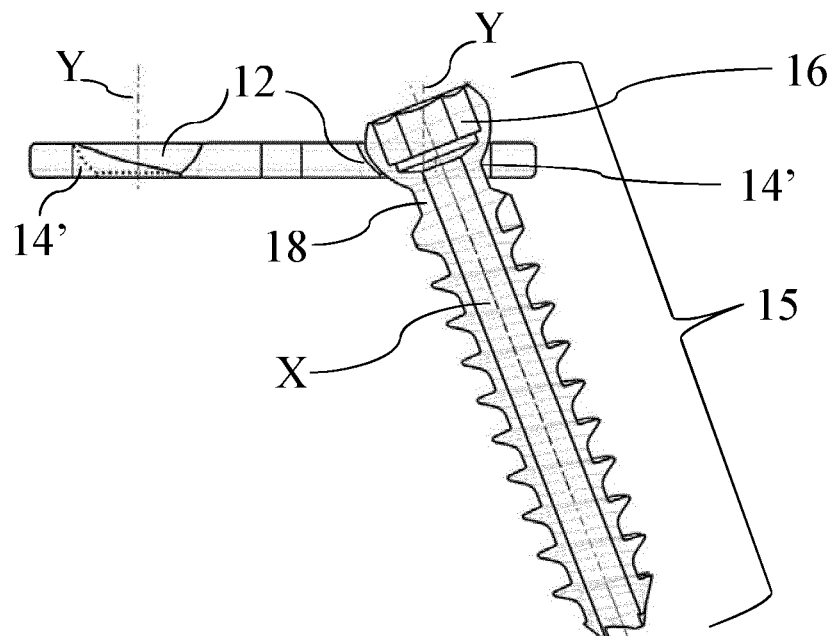
FIG. 1D is a sectional side view of the bone plate in FIG. 1A with a fixing screw inserted in a second configuration.
Figure 1E:
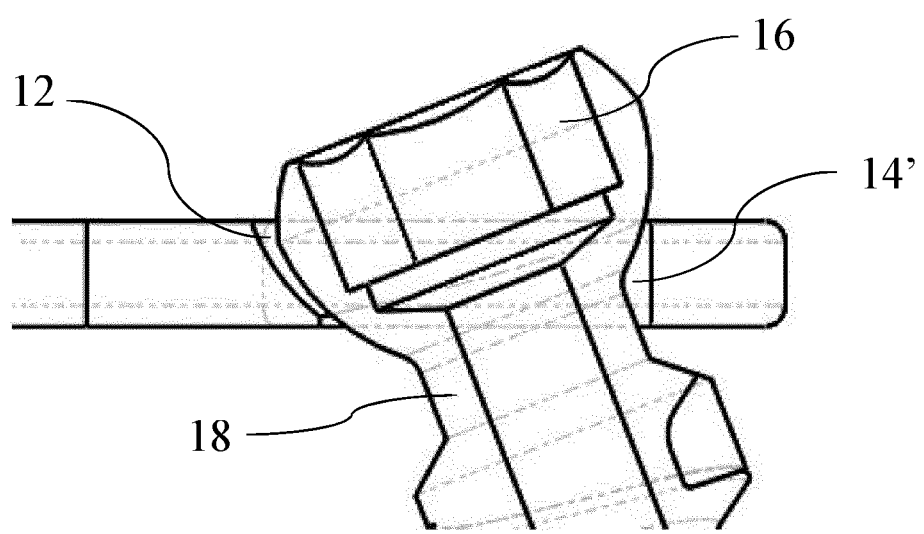
FIG. 1E is a part of FIG. 1D detailing the screw head housed within the plate.
Figure 2A:
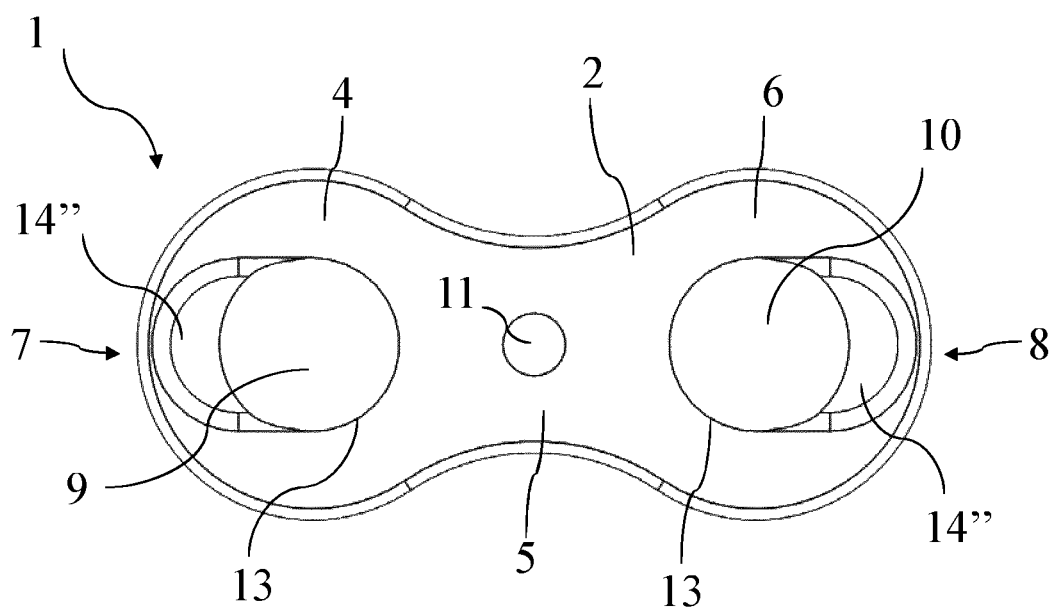
FIG. 2A is a bottom view of a bone plate according to a second embodiment.
Figure 2B:
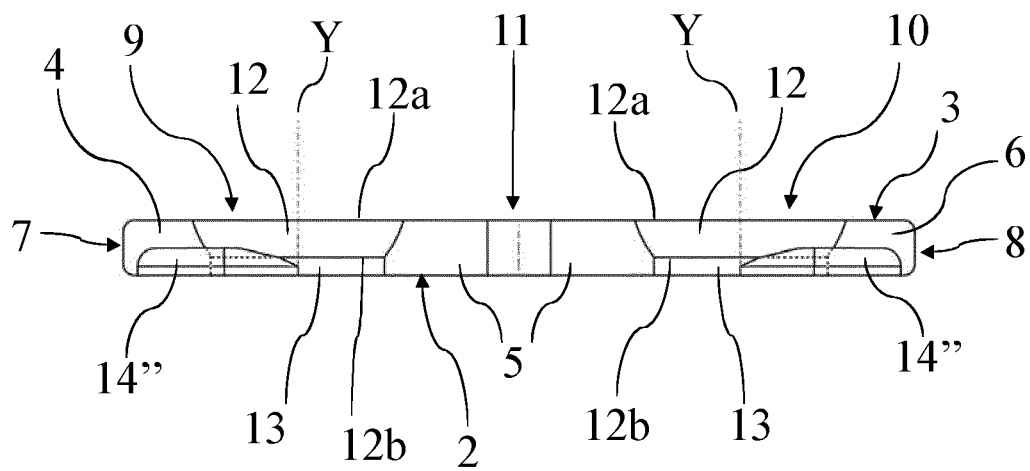
FIG. 2B is a sectional side view of the bone plate in FIG. 2A.
Figure 2C:
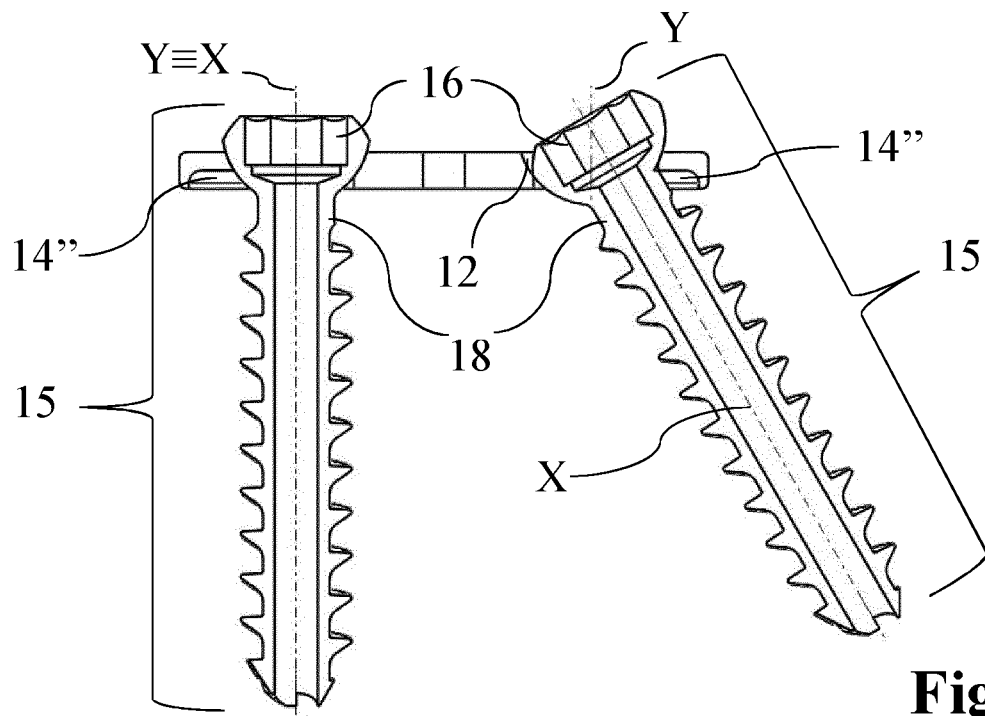
FIG. 2C is a sectional side view of the bone plate in FIG. 2A with both fixing screws inserted in a first configuration.
Figure 2D:
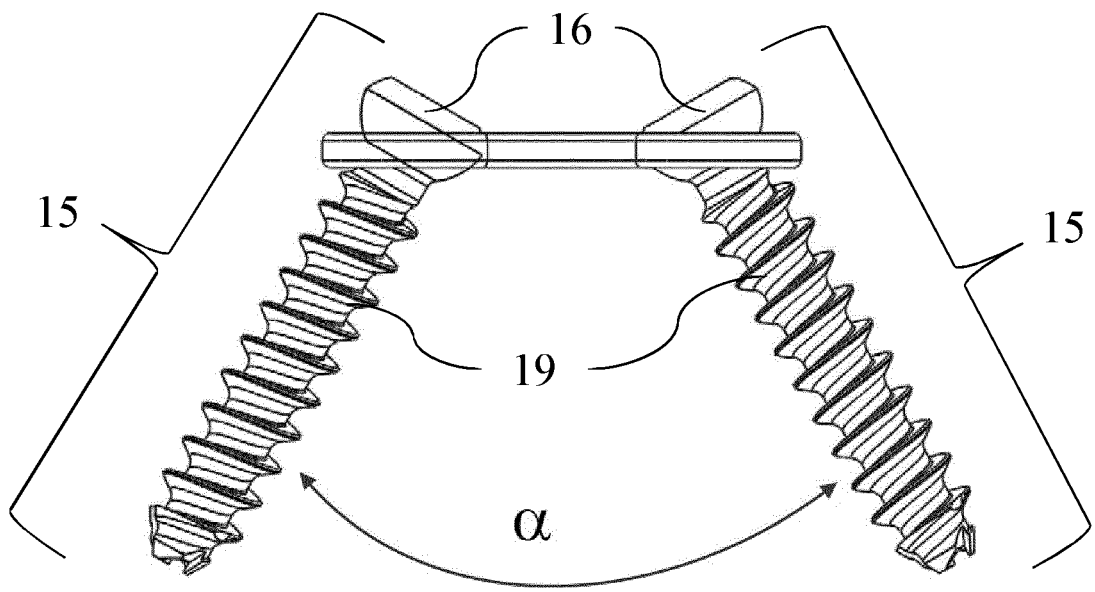
FIG. 2D is a sectional side view of the bone plate in FIG. 2A with both fixing screws inserted in a second configuration.
Figure 2E:
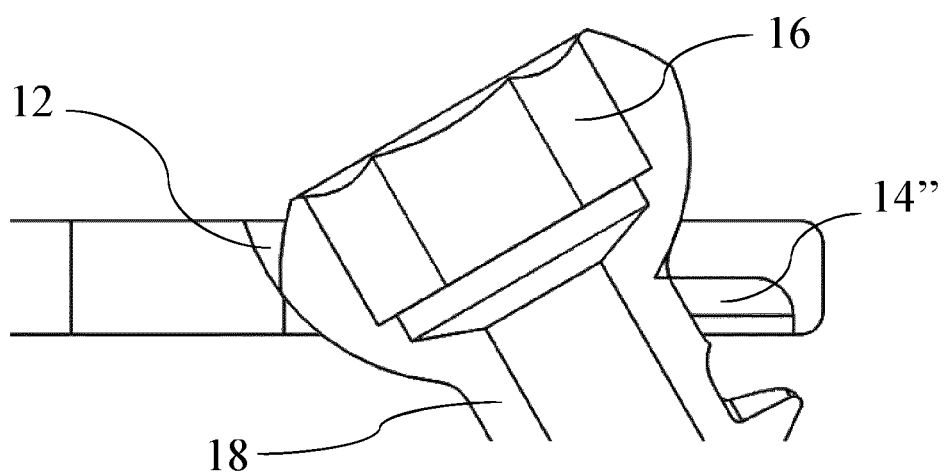
FIG. 2E is a part of FIG. 2C detailing the screw head housed within the plate.

The fixing screws 15 are firstly inserted into the openings 9 and 10 in such a way that the head 16 of the fixing screw 15 is in contact with the cup-shaped seat 12 and the axis Y of the cup-shaped seat 12 coincides with axis X of the fixing screw 15 (see FIG. 1C).

As the physeal tissue grows, the fixing screws 15 undergo a dragging action which causes a gradual angular divarication during the treatment period, i.e. rotation of the fixing screws 15 on a longitudinal plane to the bone plate 1 and away from the connecting portion 5.

The presence of the recess 14', 14", 14''', 14'''' ensures a stop contact between the shank of the fixing screw 15 and the lower edge of the openings 9 and 10, away from the connecting portion 5, i.e. at the respective ends 7 and 8.

In this way, a greater angular divarication of the fixing screws 15 is defined than that which would occur without the recess 14',14",14',14", thereby allowing the bone plate 1 and fixing screws 15 as a whole to follow the bone growth for the entire duration of the treatment.

The bone plate according to the invention solves the technical problem and delivers numerous advantages, including that of preventing breakage of the fixing screws and ensuring full correction of the bone deformation with a single surgery.

The presence of the recess prevents the fixing screws from reaching their end point too early, and so avoids the need to reposition the screws before the end of the treatment.

Advantageously, the bone plate described above has a flat shape and an even thickness with no protrusions so as to avoid friction with the soft tissue surrounding the implantation site.

Another advantage is that the aforementioned shape of the bone plate does not require complex and expensive manufacturing processes.

Furthermore, it is observed that making the bone plate according to the invention from a rigid material causes greater resistance to the stress that the device is subjected to in comparison to using a flexible material.

Obviously, a person skilled in the art may make numerous modifications and variations to the invention described above in order to satisfy particular and specific requirements, all however within the scope of protection of the invention as defined in the following claims.

The invention claimed is:

1. Bone plate for epiphysiodesis comprising: a first portion and a second portion structured to be fastened to epiphysis and metaphysis, respectively, of a long bone in a paediatric patient; said first and second portions being joined by a connecting portion structured to straddle a growth plate of said long bone; said first and said second portions being intersected by at least a first and at least a second opening, respectively, structured to receive fixing screws for fastening to said long bone; said bone plate having a bilobal figure, such as an eight shape; at least one of said first and second openings comprising: a cup-shaped seat for housing a head of said fixing screw in a tiltable manner, said cup-shaped seat having an entry section structured to allow insertion of the head of said fixing screw and an exit section of an at least locally smaller size compared to a respective size of said entry section so as to retain the head of said fixing screw; wherein the at least one of said first and second openings further comprises at least one recess which merges into the cup-shaped seat, expanding the exit section away from the connecting portion, and wherein said at least one recess takes form of a tilted hole with respect to a central axis of symmetry of said cup-shaped seat, wherein the tilted hole locally widens an outer periphery, opposite the connecting portion, of the exit section of said cup-shaped seat, and wherein the tilted hole extends from a merging point on said cup-shaped seat away from both the connecting portion and the entry section.

2. Bone plate according to claim 1, wherein said at least one of said first and second openings further comprises a cylindrical through hole, which extends said cup-shaped seat beyond said exit section opening on a first surface of the bone plate opposite a second surface on which said cup-shaped seat opens.

3. Bone plate according to claim 1, wherein said cup-shaped seat has a spherical inner shape, shaped to slidably house the head of the fixing screw which is also spherical.

4. Bone plate according to claim 1, wherein said bone plate has a symmetrical structure, at least one of said first openings and at least one of said second openings being identical and opposite each other.

5. Bone plate according to claim 4, wherein each of said first and said second portions has respectively two first openings and two second openings, said first and said second openings being aligned along transverse axes to a longitudinal extension of said bone plate.

6. Bone plate according to claim 5, wherein said bilobal figure comprises a quatrefoil shape.

7. Epiphysiodesis kit comprising:
a bone plate for epiphysiodesis comprising: a first portion and a second portion structured to be fastened to epiphysis and metaphysis, respectively, of a long bone in a paediatric patient; said first and second portions being joined by a connecting portion structured to straddle a growth plate of said long bone; said first and said second portions being intersected by at least a first and at least a second opening, respectively, structured to receive two fixing screws for fastening to said long bone; said bone plate having a bilobal figure, such as an eight shape; at least one of said first and second openings comprising: a cup-shaped seat for housing a head of said fixing screw in a tiltable manner, said cup-shaped seat having an entry section structured to allow insertion of the head of said fixing screw and an exit section of an at least locally smaller size compared to a respective size of said entry section so as to retain the head of said fixing screw; wherein at least one of said first and second openings further comprises at least one recess which merges into the cup-shaped seat expanding the exit section away from the connecting portion, and wherein said at least one recess takes form of a tilted hole with respect to a central axis of symmetry of said cup-shaped seat, wherein the tilted hole locally widens an outer periphery, opposite the connecting portion, of the exit section of said cup-shaped seat, and wherein the tilted hole extends from a merging point on said cup-shaped seat away from both the connecting portion and the entry section;
said two fixing screws with said heads, which can be inserted into said cup-shaped seat in the tiltable manner and a shank which is at least partially threaded and structured to pass through said first or said second opening, respectively, to engage with epiphysis or metaphysis respectively of the patient.

* * * * *